US00PP09912P

United States Patent [19]

Wain

[11] Patent Number: Plant 9,912

[45] Date of Patent: Jun. 3, 1997

[54] CHRYSANTHEMUM PLANT NAMED 'REGAL ABOUT TIME'

[75] Inventor: Peter Wain, Hayling Island, United Kingdom

[73] Assignee: Cleangro Ltd., Chichester, United Kingdom

[21] Appl. No.: 627,389

[22] Filed: Apr. 4, 1996

[51] Int. Cl.[6] ..... A01H 5/00

[52] U.S. Cl. ..... Plt./76

[58] Field of Search ..... Plt./76, 81, 82

[56] References Cited

U.S. PATENT DOCUMENTS

P.P. 5,350 11/1984 Duffett ..... Plt./76

P.P. 5,777 8/1986 Duffett ..... Plt./76

P.P. 6,552 1/1989 Hesse ..... Plt./76

*Primary Examiner*—Howard J. Locker

*Attorney, Agent, or Firm*—C. A. Whealy

[57] ABSTRACT

A distinct cultivar of Chrysanthemum plant named Regal About Time, characterized by its flat capitulum form; moderately vigorous and medium growth habit; freely branching plant habit; medium decorative-type inflorescences; purple ray florets; numerous inflorescences per plant; and good postproduction longevity.

1 Drawing Sheet

1

The present invention relates to a new and distinct cultivar of Chrysanthemum plant, botanically known as *Dendranthema grandiflora* and referred to by cultivar name Regal About Time.

The new cultivar is a spontaneous mutation of the commercial cultivar About Time (U.S. Plant patent application Ser. No. 08/316,947, now abandoned). The new cultivar was discovered and selected by the inventor in Havant, Hampshire, United Kingdom, as a single plant among a population of plants of the cultivar About Time. This single plant consistently formed inflorescences having purple-colored ray florets compared to the light lavender-colored ray florets of plants of the cultivar About Time.

Asexual reproduction of the new cultivar by terminal cuttings taken at Havant, Hampshire, United Kingdon, has shown that the unique features of this new Chrysanthemum are stable and reproduced true to type in successive generations.

The following traits have been repeatedly observed and are determined to be the unique characteristics of Regal About Time. These characteristics in combination distinguish Regal About Time as a new and distinct cultivar:

1. Flat capitulum form.
2. Moderately vigorous and medium growth habit.
3. Freely branching plant habit.
4. Medium decorative-type inflorescences.
5. Purple ray florets.
6. Numerous inflorescences per plant.
7. Good postproduction longevity with inflorescences maintaining good substance and color for more than 18 days in an interior environment.

The cultivar Regal About Time has not been observed under all possible environmental conditions. The phenotype may vary somewhat with variations in environment such as temperature, daylength and light intensity, without, however, any variance in genotpe.

Plants of the new Chrysanthemum are similar to the mutation parent cultivar About Time in plant habit and growth rate. However in side-by-side comparisons in Oxnard, Calif., under commercial practice, plants of the new Chrysanthemum differed from plants of the cultivar About Time in the following characteristics:

1. Plants of the new Chrysanthemum have more inflorescences per lateral branch than plants of the cultivar About Time.

2

2. Ray florets of plants of the new Chrysanthemum are purple in color, whereas ray florets of plants of the cultivar About Time are light lavender pink in color.

A detailed comparison of plants of the new Chrysanthemum and the cultivar About Time appears in Chart A at the end of the specification.

The accompanying colored photograph illustrates the overall appearance of the new cultivar, showing the colors as true as it is reasonably possible to obtain in colored reproductions of this type. The photograph comprises a top perspective view of a typical flowering 16.5-cm container of Regal About Time with five cuttings in the container and the terminal inflorescences removed (center-budded pot Chrysanthemum).

In the following description, color references are made to The Royal Horticultural Society Colour Chart except where general terms of ordinary dictionary significance are used. The following observations and measurements describe plants grown in Oxnard, Calif., under commercial practice in a glass-covered greenhouse with average night temperatures of 18° C., average day temperatures of 30° C., and light levels of 2,000 (cloudy conditions) to 9,000 (sunny conditions) footcandles.

After sticking unrooted cuttings of the new cultivar, plants received 21 long day/short nights followed by short day/long nights until flowering. Four weeks after the start of the short day/long night treatment, plants received one spray application of daminozide growth retardant at a rate of 2,500 ppm. Measurements and numeral values represent ranges or averages for six typical flowering plants.

Botanical classification: *Dendranthema grandiflora* cultivar Regal About Time.

Commercial classification: Decorative potted Chrysanthemum.

Parentage: Spontaneous mutation of *Dendranthema grandiflora* cultivar About Time (U.S. Plant patent application Ser. No. 08/316,947, now abandoned).

Propagation:

*Type.*—Terminal tip cuttings.

*Time to rooting.*—7 to 10 days with soil temperatures of 21° C.

*Rooting habit.*—Fine, Fibrous and well-branched.

Plant description:

*Appearance.*—Perennial herbaceous decorative potted plant. Stems upright, uniform habit and freely branching. Moderately vigorous and medium growth habit.

*Plant height.*—About 25 cm.

*Lateral branch length.*—16 to 18.5 cm.

*Quantity of lateral branches after removal of apical meristem.*—About 4.

*Stem color.*—147B.

*Foliage description.*—Number of leaves per lateral branch: 14 to 16. Leaf arrangement: Alternate. Leaf size, fully expanded: Length: About 10 cm. Width: About 5.5 cm. Leaf apex: Acuminate. Leaf base: Attenuate. Leaf margin: Palmately lobed. Leaf texture: Upper and under surfaces slightly pubescent, smooth and dull. Veins prominent on under surface. Petiole length: About 2 cm. Color: Young foliage upper surface: 147A. Young foliage under surface: 147B. Fully expanded foliage upper surface: 147A. Fully expanded foliage under surface: 147B. Venation upper surface: 147B. Venation under surface: 147B. Petiole: 147A.

Flowering description:

*Appearance.*—Decorative inflorescence form. Inflorescences borne on terminals above foliage, arising from leaf axils. Disc and ray florets arranged acropetally on a flat capitulum.

*Flowering response.*—Under natural conditions, plant flowers in the autumn/winter in the Northern Hemisphere. At other times of the year, inflorescence initiation and development can be induced under short day/long night conditions (at least 13.5 hours of darkness). Plants exposed to 2 to 3 weeks of long day/short night conditions after sticking followed by photoinductive short day/long night conditions, flower about 54 to 56 days later.

*Postproduction longevity.*—In an interior environment, inflorescences and foliage of flowering plants will maintain good color and substance for at least 18 days in an interior environment.

*Quantity of inflorescences.*—About 7 inflorescences per flowering stem.

*Inflorescence size.*—Diameter: About 8 cm. Depth (height): About 2.7 cm. Diameter of disc: 4 to 5 mm.

*Ray florets.*—Shape: Rounded, wide. Size: Length: About 3.5 cm. Width: About 1 cm. Apex: Rounded. Base: Acute. Margin: Entire. Texture: Satiny, smooth and glabrous. Aspect: Flat. Number of ray florets per inflorescence: About 226. Color: When opening, upper surface: 1A. When opening, under surface: 1A. Mature, upper surface: 70A fading to 70C with subsequent development. Mature, under surface: 70D.

*Disc florets.*—Shape: Tubular. Size: Length: About 5 mm. Width: About 1 mm. Number of disc florets per inflorescence: About 27. Color: Immature: 154A. Mature: 12A.

*Peduncle.*—Aspect: Strong and angled about 25° to the stem. Length: About 5.5 cm. Texture: Glabrous. Color: 147B.

*Reproductive organs.*—Androecium: Present on disc florets only. Anther color: 12A. Pollen: Moderate, 12A in color. Gynoecium: Present on both ray and disc florets. Style color: 154A.

Disease resistance: No known Chrysanthemum diseases observed to date on plants grown under commercial greenhouse conditions.

Seed production: Seed production has not been observed.

CHART A

| CHARACTERISTIC | REGAL ABOUT TIME | ABOUT TIME |
|---|---|---|
| QUANTITY OF INFLORESCENCES PER STEM | About 7 | About 5 |
| RAY FLORET COLOR, WHEN OPENING, UPPER SIDE | 1A | 1A |
| RAY FLORET COLOR, MATURE, UPPER SIDE | 70A | 69A |
| RAY FLORET COLOR, MATURE, UNDER SIDE | 70D | 69C |

It is claimed:

1. A new and distinct cultivar of Chrysanthemum plant named Regal About Time, as illustrated and described.

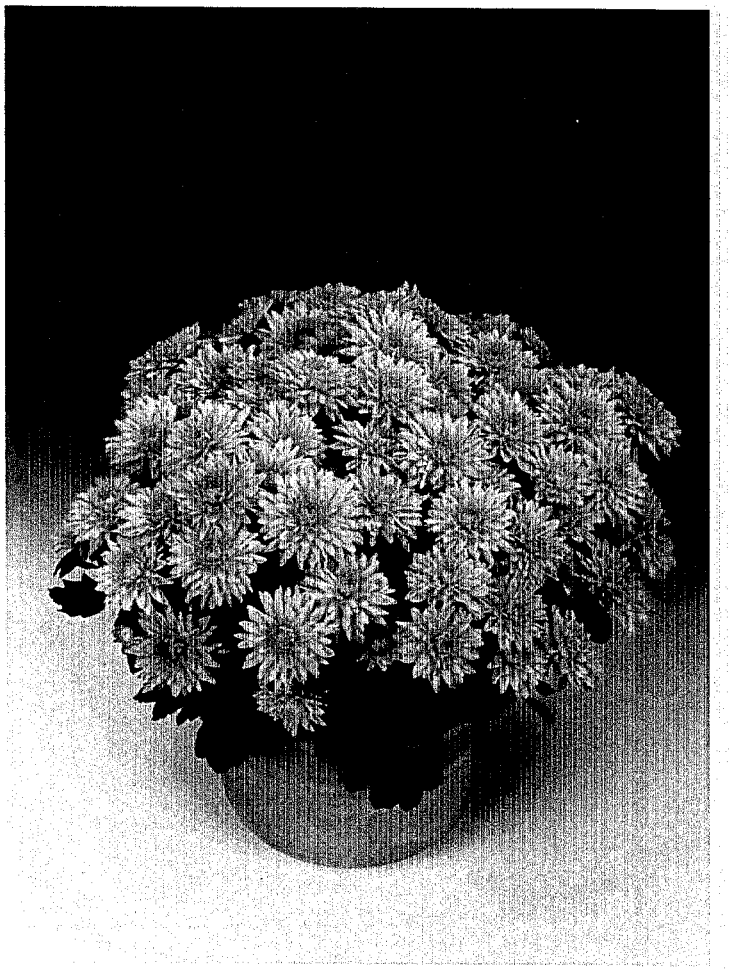

* * * * *